US010159947B2

(12) United States Patent
Köll

(10) Patent No.: US 10,159,947 B2
(45) Date of Patent: Dec. 25, 2018

(54) STIRRING DEVICE COMPRISING A MOUNTING STRUCTURE FOR A STIRRING ELEMENT AND METHOD OF MOUNTING A STIRRING ELEMENT

(71) Applicant: THÖNI INDUSTRIEBETRIEBE GMBH, Telfs (AT)

(72) Inventor: Thomas Köll, Telfs (AT)

(73) Assignee: Thöni Industriebetriebe GmbH, Telfs (AT)

( * ) Notice: Subject to any disclaimer, the term of this patent is extended or adjusted under 35 U.S.C. 154(b) by 93 days.

(21) Appl. No.: 14/911,619

(22) PCT Filed: Aug. 14, 2014

(86) PCT No.: PCT/EP2014/067393
§ 371 (c)(1),
(2) Date: Feb. 11, 2016

(87) PCT Pub. No.: WO2015/022390
PCT Pub. Date: Feb. 19, 2015

(65) Prior Publication Data

US 2016/0199797 A1 Jul. 14, 2016

(30) Foreign Application Priority Data

Aug. 16, 2013 (EP) .................................... 13180756

(51) Int. Cl.
*B01F 7/00* (2006.01)
*C12M 1/06* (2006.01)

(52) U.S. Cl.
CPC ............. *B01F 7/001* (2013.01); *C12M 27/02* (2013.01)

(58) Field of Classification Search
CPC ................................ B01F 7/001; C12M 27/02
(Continued)

(56) References Cited

U.S. PATENT DOCUMENTS 1,768,595 A 7/1930 Gilson
3,460,268 A * 8/1969 Greathouse ............ A46B 17/06 34/58

(Continued)

FOREIGN PATENT DOCUMENTS

CN 201940183 U 8/2011
EP 0 601 359 A2 6/1994

(Continued)

OTHER PUBLICATIONS

International Search Report of corresponding PCT/EP2014/067393, dated Nov. 4, 2014, 2 pages.

(Continued)

*Primary Examiner* — Anshu Bhatia
(74) *Attorney, Agent, or Firm* — Lewis Roca Rothgerber Christie LLP

(57) ABSTRACT

In accordance with embodiments of the herein disclosed subject matter it is described a stirring device (200) for a biogas fermenter wherein the stirring device (200) is configured for stirring a fermentation material and comprises a shaft (102) rotatable about an axis of rotation and a mounting structure (106) attached to the shaft (102). The mounting structure (106) has a first connection surface (112) and the second connection surface (114) and a stirring element (116) is attached to the first connection surface (112) and the second connection surface (114). The first connection surface (112) and the second connection surface (112) are located at opposite sides of the shaft (102) with the shaft being located between the first connection surface (112) and the second connection surface (114). The stirring element (116) may be configured to be spaced from the shaft (102) when the stirring element (116) is attached to the first connection surface (112) and the second connection surface (114). According to an embodiment, the stirring device (200)

(Continued)

is adapted for stirring fermentation material which is subject to dry fermentation.

11 Claims, 2 Drawing Sheets

(58) Field of Classification Search
USPC .................................................. 366/343, 342
See application file for complete search history.

(56) References Cited

U.S. PATENT DOCUMENTS

2005/0195682 A1 9/2005 Swisher
2008/0248519 A1* 10/2008 Friedmann .......... B01F 7/00633 435/41

FOREIGN PATENT DOCUMENTS

| | | | |
|---|---|---|---|
| EP | 1 841 853 | | 10/2007 |
| EP | 2 656 909 | A1 | 10/2013 |
| GB | 1 215 057 | | 12/1970 |
| WO | WO 2006/079228 | A1 | 8/2006 |

OTHER PUBLICATIONS

First Office action issued by the State Intellectual Property Office of People's Republic of China (SIPO) for Application No. 201480045509.6 dated Jan. 24, 2017; 6 pages (English translation provided).

* cited by examiner

STIRRING DEVICE COMPRISING A MOUNTING STRUCTURE FOR A STIRRING ELEMENT AND METHOD OF MOUNTING A STIRRING ELEMENT

CROSS-REFERENCED TO RELATED APPLICATION(S)

This Application is a National Phase Patent Application and claims priority to and the benefit of International Application Number PCT/EP2014/067393, filed on Aug. 14, 2014, which claims priority to and the benefit of European Patent Application No. 13180756.2, filed Aug. 16, 2013, the entire contents of all of which are incorporated herein by reference.

FIELD OF INVENTION

The present invention relates to the field of stirring devices for a biogas fermenter.

BACKGROUND

EP 1841853 B1 discloses a horizontal plug flow fermenter consisting of a tank and a driven shaft penetrating in the tank in its longitudinal direction. The driven shaft comprises a plurality of agitator arms arranged thereon with paddles. The agitator arms rest on the shaft and are laterally supported by means of flange plates.

SUMMARY

In view of the above-described situation, there exists a need for an improved technique that enables to provide a stirring device for a biogas fermenter which provides for an efficient and reliable mounting of stirring elements to a rotatable shaft of the stirring device, while substantially avoiding or at least reducing one or more of the above-identified problems.

This need may be met by the subject matter according to the independent claims. Advantageous embodiments of the herein disclosed subject matter are described by the dependent claims.

According to an embodiment of a first aspect of the herein disclosed subject matter there is provided a stirring device for a biogas fermenter (e.g. a plug flow fermenter), the stirring device being configured for stirring a fermentation material, the stirring device comprising: a shaft rotatable about an axis of rotation; a mounting structure attached to the shaft, the mounting structure having a first connection surface and a second connection surface; a stirring element attached to the first connection surface and the second connection surface; wherein the first connection surface and the second connection surface are located at opposite sides of the shaft with the shaft being located between the first connection surface and a second connection surface.

This aspect of the herein disclosed subject matter is based on the idea that providing of connection surfaces at opposite sides of the shaft allows to position the stirring element (e.g. a stirring paddle) on the connection surfaces which facilitates attachment of the stirring element to the shaft. In particular, in an embodiment, for mounting of the stirring element the shaft is rotated into an angular position such that the first connection surface and the second connection surface, to which a stirring element is to be attached, point vertically upwards (against the direction of gravity). Hence the paddle rests save on the connection surfaces before its attachment thereto. Further, the connection surfaces at opposite sides of the shaft provided a good force distribution in the shaft. To this end, it should be borne in mind that during stirring a fermentation material in a biogas fermenter, and in particular in a plug flow fermenter, high forces are transferred to the shaft by the individual stirring elements.

Although herein reference is usually made to a single stirring element, it should be understood that the stirring device usually includes a plurality of stirring elements. According to an embodiment, the mounting structures for the stirring elements are attached to the shaft at the manufacturer's premises and each individual stirring element is attached to its mounting structure at the construction site. Hence, the time required for assembly of the stirring device at the construction site is reduced.

The stirring device according to embodiments of the herein disclosed subject matter is in particular suitable for plug flow fermenters and fermenters for dry fermentation wherein the fermentation material has a dry substance content of e.g. 15% or more, e.g. of 20% or more, e.g. of 25% or more or 30% or more.

According to a further embodiment the mounting structure comprises a first element and a second element spaced apart from each other in circumferential direction about the axis of rotation, the first element having the first connection surface and the second element having the second connection surface. According to an embodiment, the first element and the second element are individual elements which are not connected. According to other embodiments, the mounting structure may be a single piece which provides the first connection surface and the second connection surface.

According to an embodiment, the first connection surface and the second connection surface define a connection plane, the connection plane intersecting the shaft.

According to a further embodiment, each of the first connection surface and the second connection surface comprises two surface portions spaced apart from each other in axial direction. This may improve the mechanical stability of the joint between the stirring element and the connection surfaces. Further, the spaced apart surface portions of the connection surface may provide efficiency regarding mechanical stability and material consumption.

According to an embodiment, the first connection surface and the second connection surface are spaced from the shaft. Spacing the connection surfaces from the shaft allows to design force transfer elements, which are configured for transferring the force between the stirring element and the shaft (such as the mounting parts discussed below), independently from the connection surfaces. Further, spacing the connection surfaces from the shaft may facilitate attachment of the stirring element to the connection surfaces.

According to an embodiment, the mounting structure comprises, for each of the first connection surface and the second connection surface, a first mounting part attached to the shaft, a second mounting part attached to the shaft, and an intermediate part extending between the first mounting part and the second mounting part, wherein the intermediate part is spaced from the shaft. For example, according to an embodiment, each of the first element and the second element comprises a first mounting part attached to the shaft, a second mounting part attached to the shaft, and an intermediate part extending between the first mounting part and the second mounting part. According to an embodiment, the first mounting part and the second mounting part are configured for being welded to the shaft. According to an embodiment, the first mounting part and the second mounting part are spaced apart in axial direction. Spaced apart mounting parts which are welded to the shaft reduce an influence on the shaft due to the welding. Such an influence may be distortion, local alloy composition, etc.

According to an embodiment, each intermediate part provides one of the first connection surface and the second connection surface. Hence, according to an embodiment each of the first element and the second element of the mounting structure includes a first mounting part, a second mounting part and an intermediate part. According to an embodiment, the first element is formed of a single piece and/or the second element is formed of a single piece. For example, in an embodiment the first mounting part, the second mounting part and the intermediate part of an element (first and/or second element) are integrally formed from a single piece. According to another embodiment the first element and/or the second element is formed of at least two separate parts attached to each other. For example, in an embodiment, the first mounting part, the second mounting part and the intermediate part of an element (first and/or second element) are separate components attached to each other to form the respective element.

According to an embodiment, the first mounting part extends over a first angular range, the second mounting part extends over a second angular range and the first angular range and the second angular range overlap each other. An overlap between the angular ranges over which the first mounting part and the second mounting part (of an element) extend may result in an advantageous force distribution in the shaft. According to an embodiment, the first mounting part and the second mounting part are in alignment in axial direction. Generally herein, the term “axial direction” refers to the direction parallel to the shaft and its axis of rotation, unless otherwise noted.

According to an embodiment, the first mounting part, the second mounting part and the intermediate part are separate components wherein the intermediate part is attached to the first mounting part and the second mounting part. This may facilitate attachment of the mounting structure to the shaft. For example, the first mounting part and the second mounting part may be attached to the shaft before the intermediate part is attached to the first mounting part and the second mounting part. This may facilitate the attachment procedure in which according to an embodiment first only two spaced apart mounting parts are attached to the shaft. After attachment of the first mounting part and the second mounting part, according to an embodiment the intermediate part is positioned with respect to the first mounting part and the second mounting part (optionally using of a template) and is then attached thereto. This may provide an increased precision of the position of the first connection surface and the second connection surface.

According to an embodiment, the attachment operations are performed simultaneously on both opposite sides of the shaft. For example, according to an embodiment the first mounting part of the first element of the mounting structure and the first mounting part of the second element of the mounting structure are attached to the shaft simultaneously. Simultaneous attachment of opposing mounting parts on the shaft may reduce the influence of the attachment of the mounting parts to the shaft. According to an embodiment, opposing mounting parts of the first element and the second element of the mounting structure are at the same axial position or are at least close in axial position.

According to an embodiment, the stirring device comprises a first protrusion extending in circumferential direction over the extent of the intermediate part at its connection surface; the first protrusion connecting the first mounting part and the intermediate part; a second protrusion extending in circumferential direction over the extent of the intermediate part at its connection surface; the second protrusion connecting the second mounting part and the intermediate part. The protrusion extending in circumferential direction and connecting one of the mounting parts with the associated intermediate part improves the force distribution on the respective mounting part to which the protrusion connects the intermediate part. According to an embodiment, the protrusion is provided on the intermediate part. For example, according to an embodiment the protrusion and the intermediate part form of a single piece. According to other embodiments, the protrusion may be provided by a separate part, for example a piece of sheet metal which has suitable dimensions. Attachment of the mounting part, the sheet metal forming the protrusions and the intermediate part may be provided by any suitable means, e.g. by welding.

According to an embodiment, the intermediate part has a circumferentially extended portion located between the two surface portions of the intermediate part. The circumferentially extended portion may increase the mechanical stability of the mounting structure without increasing the surface of the mounting structure transverse to the circumferential direction.

According to an embodiment, the circumferentially extended portion comprises a recess, the recess reducing weight of the intermediate part. For example, according to an embodiment the recess may extend through the intermediate part in radial direction, thereby forming a through hole extending through the intermediate part in radial direction. According to an embodiment, the recess is provided in the center of the circumferentially extended portion. In this way, the influence of the recess on the structural integrity of the intermediate part is kept low.

According to an embodiment, the stirring element is spaced from the shaft. In other words, according to an embodiment the stirring element is configured with regard to the shaft and the mounting structure such that the stirring element is spaced from the shaft when being mounted to the first connection surface and the second connection surface. The stirring element being spaced from the shaft has the effect that no forces are transferred directly from the stirring element to the shaft. Rather, in accordance with an embodiment, force transfer occurs only via the mounting structure. This allows for a well-defined design of the force transfer between the stirring element and the shaft.

According to an embodiment, the stirring element comprises a first leg, a second leg and a body; the body being connected to the first leg and the second leg; the first leg being connected to the first connection surface and the second leg being connected to the second connection surface. By means of the first leg and the second leg, attachment of the body to the first connection surface and the second connection surface may be facilitated.

According to an embodiment, the stirring device comprises a guidance configured for defining a position of the stirring element with respect to the first connection surface and the second connection surface if the stirring element is in contact with the first connection surface and the second connection surface. The guidance may include one or more guide elements. Each guide element may include a first part at the mounting structure and a second part at the stirring element wherein the first part and the second part of the guide element work together to guide the stirring element into a defined position when the stirring element approaches the first connection surface and the second connection surface. Guide elements may include protrusions and corresponding recesses, etc. According to an embodiment, the guidance is configured for guiding and/or centering the stirring element during approaching the first connection surface and the second connection surface with the stirring element.

According to a further embodiment, the stirring device comprises a first form-locked join between the stirring element and the first connection surface; and, optionally a second form-locked join between the stirring element and the second connection surface. Hence, the join between the stirring element and the (first and/or second) connection surfaces may not only be fiction-locked but also form-locked. According to an embodiment, the first form-locked join is configured for transferring forces, acting in the plane of the first connection surface, between the stirring element and the first connection surface; and the second form-locked join is configured for transferring forces, acting in the plane of the second connection surface, between the stirring element and the second connection surface. For example, according to an embodiment the guidance may be configured for also providing the form-lock of the join between the stirring element and the respective connection surface.

According to an embodiment of a second aspect of the herein disclosed subject matter there is provided a method of mounting a stirring element to a shaft of a stirring device, the method comprising attaching a mounting structure to the shaft, the mounting structure having a first connection surface and a second connection surface, wherein the first connection surface and the second connection surface are located at opposite sides of the shaft with the shaft being located between the first connection surface and a second connection surface; attaching a stirring element to both, the first connection surface and the second connection surface.

According to embodiments of the second aspect, the method is adapted for providing the functionality of one or more of the aforementioned embodiments and/or for providing the functionality as required by one or more of the aforementioned embodiments, in particular of the embodiments of the first aspect. For example, also any method related feature which is described with regard to the first aspect or an embodiment thereof further defines a respective embodiment of the second aspect.

According to an embodiment of a third aspect of the herein disclosed subject matter a stirring device for a biogas fermenter is provided, the stirring device being configured for stirring a fermentation material, the stirring device comprising a shaft and a plurality of stirring elements attached to the shaft; the plurality of stirring elements being configured differently in different axial portions of the shaft.

According to an embodiment, the shaft has, in axial direction, two supported portions and an intermediate portion between the two supported portions; wherein the supported portions are located closer to a support of the shaft than the intermediate portion; and wherein the length of the stirring elements in the intermediate portion of the shaft is reduced compared to the length of stirring elements in the supported portions of the shaft.

This embodiment is based on the idea that a deflection of the shaft in the intermediate portion of the shaft, e.g. due to the weight of the shaft, is not avoided but rather the deflection is taken into account by a reduced length of the stirring elements, thus avoiding a contact between the stirring elements and the biogas fermenter.

In this regard it is noted that the term "the shaft has . . . two supported portions" does not exclude the shaft from having more than two supported portions with an intermediate portion between each two of the supported portions. Accordingly, in accordance with an embodiment, the shaft has, in axial direction, three or more of the supported portions.

According to a further embodiment the length of the stirring elements in the intermediate portion is also adapted to a buoyancy of the shaft in the fermentation material.

According to a further embodiment, at least one stirring element in an input region of the biogas fermenter is adapted to stirring fresh material introduced into the input region. According to an embodiment, in the input region of the biogas fermenter the stirring device may have a higher value of stirring cross section per unit length of the shaft in axial direction. For example, according to an embodiment, in the input region the density of stirring elements per unit length of the shaft in axial direction is higher compared to another region the fermenter. In a further embodiment, in the input region two or more stirring elements are provided in the same axial position. According to a further embodiment, an axial distance between axially neighboring stirring elements in the input region is reduced compared to another region of the fermenter. According to a further embodiment, an angular distance between axially neighboring stirring elements in the input region is reduced compared to another region the fermenter. According to a further embodiment, in the input region the stirring element are configured such that the stirring cross section per stirring element is higher compared to another region of the fermenter. This may be achieved by a larger head of the stirring elements in the input region. In this regard it is noted that in accordance with an embodiment, the stirring element has a body as described herein and a head at a radially outer end of the body, wherein the head has, in axial direction, an increased width in compared to the body.

According to a further embodiment, at least one stirring element is adapted for transporting sentiment in circumferential direction. For example, according to embodiments of the herein disclosed subject matter, the stirring element may have different recesses e.g. regarding width (in axial direction), height (perpendicular to the axial direction and perpendicular to the circumferential direction), depth (in circumferential direction), radial depth profiles.

According to a further embodiment, at least one stirring element in an output region of the biogas fermenter is adapted to reduce sediment in the output region. For example, according to an embodiment the at least one stirring element in the output region of the biogas fermenter (or, in another embodiment the head of the stirring element) may have larger axial and/or radial extent compared to the other stirring elements of the plurality of stirring elements.

According to further embodiments of the third aspect, the stirring device is adapted for providing the functionality of one or more of the aforementioned embodiments and/or for providing the functionality as required by one or more of the aforementioned embodiments, in particular of the embodiments of the first and the second aspect.

According to an embodiment of a fourth aspect of the herein disclosed subject matter, a stirring device for a biogas fermenter is provided, the stirring device being configured for stirring a fermentation material, the stirring device comprising a shaft and a plurality of stirring elements attached to the shaft; a first stirring element of the plurality of stirring elements sweeping over a first axial range of the biogas fermenter and a second stirring element of the plurality of stirring elements sweeping over a second axial range of the biogas fermenter; wherein the first axial range and the second axial range contact each other.

In this regard it is noted that the reference to a first and a second stirring element sweeping over respective first and second axial ranges does not exclude the stirring device having three or more stirring elements, each of which has its sweeping range. In particular, usually the stirring device may have a plurality of stirring elements, e.g. 20 or more.

The fourth aspect of the herein disclosed subject matter is based on the idea that a formation of sediment in the biogas fermenter can be avoided or at least be reduced if axial gaps between the sweeping ranges of the stirring elements are avoided.

According to an embodiment of the fourth aspect, the first axial range and the second axial range overlap each other. According to further embodiments, each of the plurality of stirring elements sweeps over an axial range (i.e. has an axial sweeping range) which contacts or overlaps the axial sweeping range of the neighboring stirring elements.

According to a further embodiment of the fourth aspect, a mounting structure as described with regard to the first and the second aspect is provided for each of the stirring elements. According to a further embodiment, the mounting structures of axially neighboring stirring elements overlap each other in axial direction. However, in another embodiment where the stirring elements have a sufficient axial sweeping range, the overlap of the mounting structures is not necessary and is not realized.

According to a further embodiments of the fourth aspect, the stirring device is adapted for providing the functionality of one or more of the aforementioned embodiments and/or for providing the functionality as required by one or more of the aforementioned embodiments, in particular of the embodiments of the first, the second and the third aspect.

In the above there have been described and in the following there will be described exemplary embodiments of the subject matter disclosed herein with reference to a stirring device for a biogas fermenter and a method of mounting a stirring element to a shaft of a stirring device of a biogas fermenter. It has to be pointed out that of course any combination of features relating to different aspects of the herein disclosed subject matter is also possible. In particular, some features have been or will be described with reference to apparatus type embodiments whereas other features have been or will be described with reference to method type embodiments. However, a person skilled in the art will gather from the above and the following description that, unless otherwise notified, in addition to any combination of features belonging to one aspect also any combination of features relating to different aspects or embodiments, for example even combinations of features of apparatus type embodiments and features of the method type embodiments are considered to be disclosed with this application.

The aspects and embodiments defined above and further aspects and embodiments of the herein disclosed subject matter are apparent from the examples to be described hereinafter and are explained with reference to the drawings, but to which the invention is not limited. Statements and explanations given above are also valid for the description of the examples given below and vice versa.

DETAILED DESCRIPTION

Figure 1:
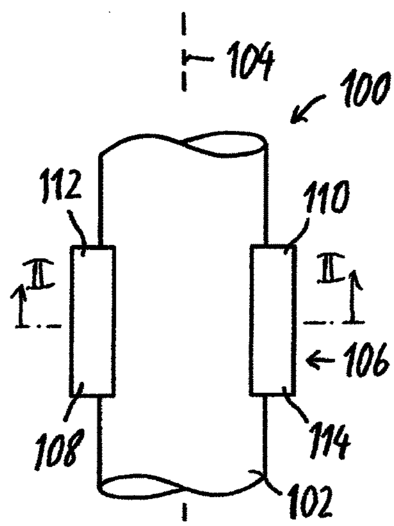
FIG. 1 shows part of a stirring device for a biogas fermenter according to embodiments of the herein disclosed subject matter.

The illustration in the drawings is schematic. It is noted that in different figures, similar or identical elements are provided with the same reference signs or with reference signs, which are different from the corresponding reference signs only within the first digit. Accordingly, the description of similar or identical features is not repeated in the description of subsequent figures in order to avoid unnecessary repetitions. However, it should be understood that the description of these features in the preceding figures is also valid for the subsequent figures unless noted otherwise.

FIG. 1 shows part of a stirring device 100 for a biogas fermenter according to embodiments of the herein disclosed subject matter.

The stirring device comprises a shaft 102 which is rotatable about an axis of rotation 104. According to an embodiment, the shaft 102 is a hollow shaft, as shown in FIG. 1. Attached to the shaft 102 is a mounting structure 106 with a first element 108 and a second element 110. The first element 108 comprises a first connection surface 112 and the second element 110 comprises a second connection surface 114. The first connection surface 112 and the second connection surface 114 are located at opposite sides of the shaft 102 with the shaft 102 being located between the first connection surface 112 and the second connection surface 114.

The first connection surface 112 and the second connection surface 114 are configured for receiving a stirring element (not shown in FIG. 1).

Figure 2:
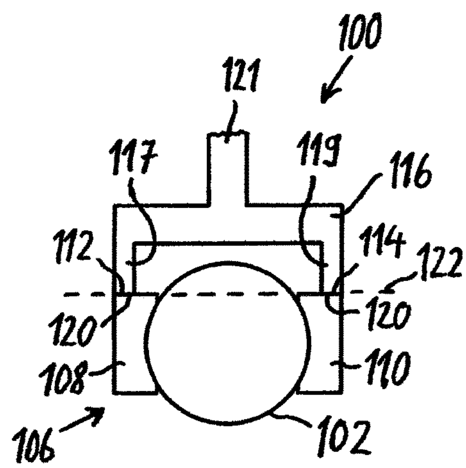
FIG. 2 shows a cross-sectional view of the stirring device of FIG. 1 along line II-II.

FIG. 2 shows a cross-sectional view of the stirring device 100 of FIG. 1 along line II-II.

FIG. 2 shows in part a stirring element 116 attached to the mounting structure 106. In particular, the stirring element 116 is attached to the first connection surface 112 and the second connection surface 114. To this end, the stirring element 116 has opposing surfaces 120 which contact the first connection surface 112 and the second connection surface 114, respectively.

In accordance with an embodiment, the stirring element 116 comprises a first leg 117, a second leg, 119, and a body 121. The body 121 is connected to the first leg 117 and the second leg 119. Further, the first leg 117 is connected with its opposing surface 120 to the first connection surface 112 and the second leg 119 is connected with its opposing surface 120 to the second connection surface 114.

In accordance with an embodiment, the first connection surface 112 and the second connection surface 114 are spaced from the shaft 102 and define a plane 122 which intersects the shaft 102.

According to an embodiment, each of the first element 108 and the second element 110 is formed as a solid, integral part. According to other embodiments, the first element and the second element may be formed of a plurality of parts.

While according to an embodiment shown in FIG. 2 the first element 108 and the second element 110 are formed as separate pieces which are as such not connected to each other, according to other embodiments the first element 108 and the second element 110 may be interconnected (not shown in FIG. 2).

Figure 3:
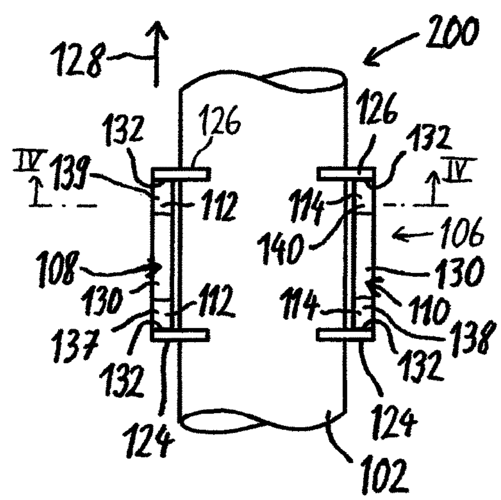
FIG. 3 shows a further stirring device for a biogas fermenter according to embodiments of the herein disclosed subject matter.

FIG. 3 shows a further stirring device 200 for a biogas fermenter according to embodiments of the herein disclosed subject matter.

In accordance with embodiments of the herein disclosed subject matter the mounting structure 106 shown in FIG. 3 comprises a first connection surface 112 and a second connection surface 114, which are located at opposite sides of a shaft 102. However, the first element 108 and the second element 110 providing the first connection surface 112 and the second connection surface 114 are different from the ones shown in FIG. 1.

According to an embodiment shown in FIG. 3 each of the first element 108 and the second element 110 comprises a first mounting part 124 and a second mounting part 126. The first mounting part 124 and the second mounting part 126 are attached to the shaft 102, e.g. by welding. It should be understood that any other suitable attachment process may be suitable for attaching the first and second mounting parts 124, 126 to the shaft 102. The first mounting part 124 and that the second mounting part 126 are spaced in axial direction 128. Between the first mounting part 124 in the second mounting part 126 an intermediate part 130 is provided which extends between the first mounting part 124 and the second mounting part 126.

According to an embodiment, the first mounting part 124, the second mounting part 126 and the intermediate part 130 are separate components. According to an embodiment, the first mounting part 124 and the second mounting part 126 have respective attachment surfaces 132 facing each other. According to an embodiment, the intermediate part 130 is attached to the attachment surfaces 132. According to other embodiments, the intermediate part 130 may be attached to other portions of the first mounting part 124 and the second mounting part 126.

In accordance with an embodiment the first connection surface 112 comprises two surface portions 137, 139 spaced apart from each other in axial direction 128. Further, the second connection surface 114 comprises two surface portions 138, 140 spaced apart from each other in the axial direction 128.

Figure 4:
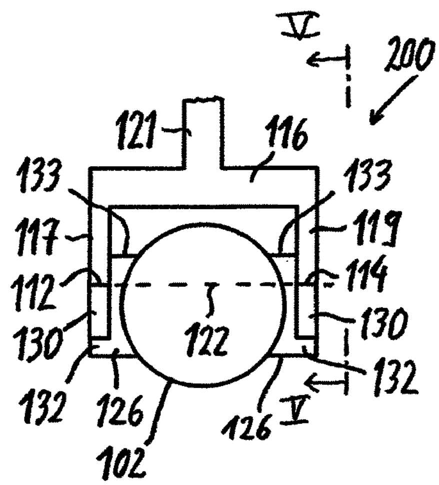
FIG. 4 shows a cross-sectional view of the stirring device of FIG. 3 along line IV-IV.

FIG. 4 shows a cross-sectional view of the stirring device 200 of FIG. 3 along line IV-IV.

In accordance with an embodiment, each intermediate part 130 provides one of the first connection surface 112 and the second connection surface 114, as shown in FIG. 3. By using the first mounting part 124 (not shown in FIG. 4) and the second mounting part 126 for the connection to the shaft 102 and on the other hand providing the intermediate part 130 for a connection to the stirring element 116, the connection plane 122 may be located closer to the axis of rotation while the first mounting part 124 and the second mounting part 126 are connected to the shaft 102 over a relatively large angular range, as shown for the second mounting part 126 in FIG. 4. Generally, this may be achieved by the first connection surface 112 and the second connection surface 114 being spaced from a circumferential edge 133 of its associated mounting part 124, 126, wherein the connection surface 112, 114 faces the circumferential edge 133.

Figure 5:
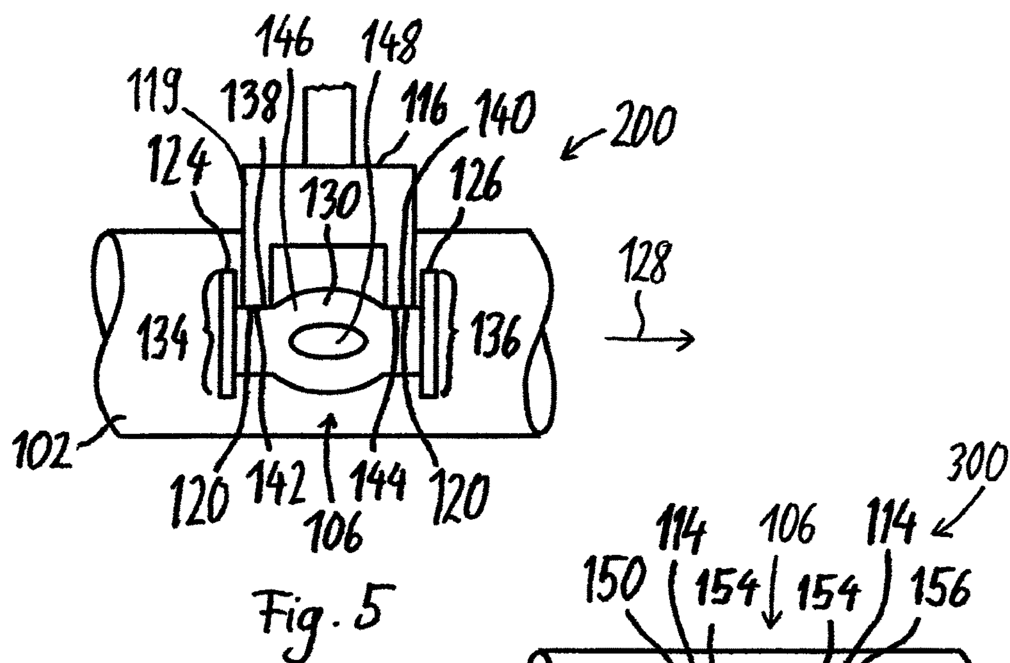
FIG. 5 shows a side view of the stirring device of FIG. 4 when viewed from line V-V.

FIG. 5 shows a side view of the stirring device 200 of FIG. 4 when viewed from line V-V.

In accordance with an embodiment, the first mounting part 124 extends over a first angular range, indicated at 134 in FIG. 5 and the second mounting part 126 extends over the second angular range, indicated at 136 in FIG. 5. According to an embodiment, the first angular range 134 and the second angular range 136 overlap each other. For example, in an embodiment the first angular range 134 and the second angular range 136 are identical, as shown in FIG. 4. In other words, in this embodiment the first mounting part 124 in the second mounting part 126 are aligned with each other in axial direction.

In accordance with an embodiment, the second leg 119 of the stirring element 116 is attached to the first surface portion 138 and the second surface portion 140 of the second connection surface 114. In accordance with a further embodiment, and as described above, the second leg 119 comprises an opposing surface 120 which is attached to the second connection surface 114 of the second element 110 of the mounting structure 106. In accordance with an embodiment, the opposing surface 120 has two surface portions 142, 144 which are spaced from each other in axial direction 128 and which are configured to be attached to the respective surface portions 138, 140 of the second connection surface 114. Likewise the opposing surface 118 of the first leg 117 of the stirring element 116 has two surface portions which are spaced from each other in axial direction (not shown in FIG. 5).

In accordance with an embodiment, the intermediate part 130 has a circumferentially extended portion 146 between the two spaced apart surface portions 138, 140 of the second connection surface 114 of the intermediate part 130. In accordance with an embodiment, the circumferentially extended portion 146 comprises a recess 148 in the form of a through hole in order to reduce the weight of the intermediate part 130.

Figure 6:
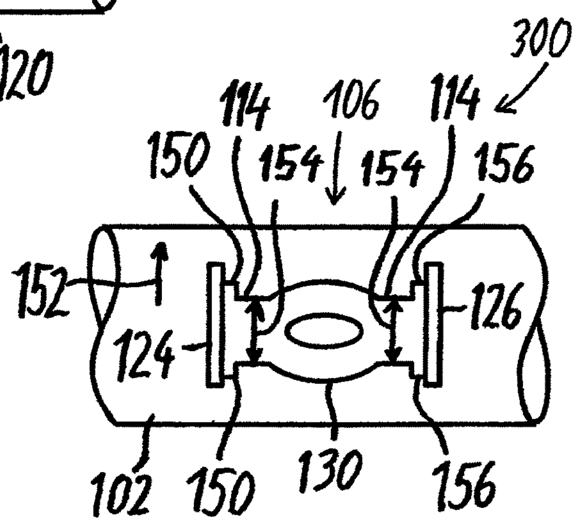
FIG. 6 shows further stirring device according to embodiments of the herein disclosed subject matter.

FIG. 6 shows further stirring device 300 according to embodiments of the herein disclosed subject matter.

According to an embodiment, the stirring device 300 comprises a mounting structure 106 which comprises a first protrusion 150 extending in circumferential direction 152 over the extent 154 of the intermediate part 130 at its connection surface 114. The first protrusion 150 connects the first mounting part 124 and the intermediate part 130. In accordance with an embodiment, the first protrusion 150 is an integral portion of the intermediate part 130, as shown in FIG. 6. According to other embodiments (not shown in FIG. 6), the protrusion 150 may be provided by a separate part located between the first mounting part 124 and the intermediate part 130. According to an embodiment, the mounting structure 106 comprises two first protrusions 150 each extending in one of the two circumferential directions (clockwise and counterclockwise), as shown in FIG. 6.

According to an embodiment, the mounting structure 106 and further comprises a second protrusion 156 extending in circumferential direction 152 over the extent 154 of the intermediate part 130 at its connection surface 114. The second protrusion 156 connects the second mounting part 126 and the intermediate part 130. The second protrusion 156 may be configured similar or identical to the first protrusion 150. According to an embodiment, a second protrusion 156 is provided for each of the two circumferential directions, as shown in FIG. 6.

Figure 7:
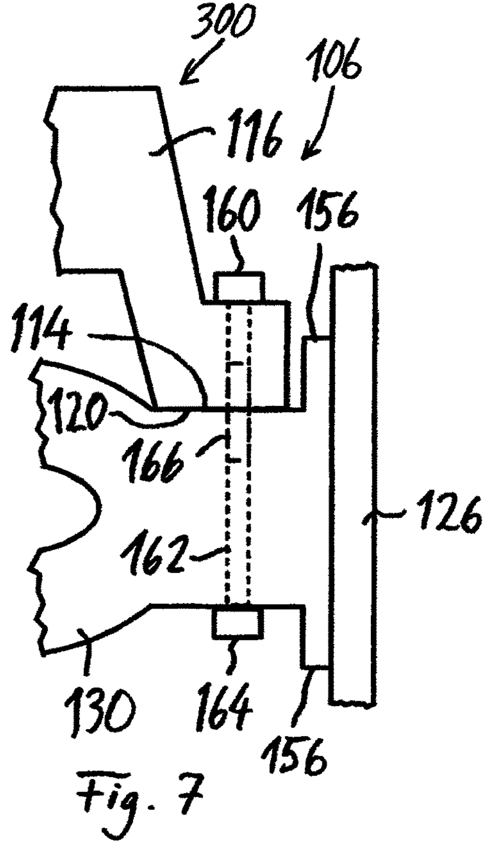
FIG. 7 shows the mounting structure of the stirring device in FIG. 6 in greater detail with the stirring element attached to the mounting structure.

FIG. 7 shows the mounting structure 106 of FIG. 6 in greater detail with the stirring element 116 attached to the mounting structure 106.

According to an embodiment, the stirring element 116 is attached to the second connection surface 114 with a bolt connection 160. The bolt connection 160 may include e.g. thread in the intermediate part 130. According to another embodiment, the bolt connection 160 may include a threaded bolt 162 with the retaining ring 164, wherein the threaded bolt extends through both, the stirring element 116 and the intermediate part 130.

According to an embodiment, the mounting structure 106 comprises a guidance 166, e.g. in the form of a drill bush as shown in FIG. 7, wherein the guidance is configured for defining a position of the stirring element 116 with respect to the second connection surface 114 if the stirring element is in contact with the first connection surface (not shown in FIG. 7) and the second connection surface 114. According to an embodiment a guidance is also provided for the first connection surface (not shown in FIG. 7). Further, while in FIG. 7 a guidance 166 is shown for the second surface portion 140 of the second connection surface 114, it should be understood that according to an embodiment a guidance is also provided for the first surface portion 138 of the second connection surface 114 as well as for the surface portions 137, 139 of the first connection surface 112 (see e.g. FIG. 3). According to an embodiment, the guidance 166, e.g. the drill bush, also provides form-locked join between the stirring element and the respective connection surface. In particular, the guidance 166 shown in FIG. 7 provides for a form-locked join between the stirring element 116 and the respective connection surface 114 and the transfers lateral forces between the stirring element 116 and the connection surface 114, e.g. if the friction between respective connection surface 114 and its opposing surface 120 is not sufficient for the force transfer.

Having regard to the subject matter disclosed herein, it should be mentioned that generally each of the first connection surface and the second connection surface may be configured according to one or more of the embodiments disclosed herein for one of these surfaces.

It should be noted that any entity disclosed herein (e.g. parts, portions, surfaces, components, units, structures and devices) are not limited to a dedicated entity as described in some embodiments. Rather, the herein disclosed subject matter may be implemented in various ways and with various granularity while still providing the specified functionality. Further, it should be noted that according to embodiments a separate entity (e.g. part, portion, surface, component, unit, structure or device) may be provided for each of the functions disclosed herein. According to other embodiments, an entity (e.g. part, portion, surface, component, unit, structure or device) is configured for providing two or more functions as disclosed herein. According to still other embodiments, two or more entities (e.g. part, portion, surface, component, unit, structure or device) are configured for providing together a function as disclosed herein.

Generally herein, and attachment of two pieces to each other may be performed by any suitable means, including one or more of welding, gluing, bolting, riveting, etc.

It should be noted that the term "comprising" does not exclude other elements or steps and the "a" or "an" does not exclude a plurality. Also elements described in association with different embodiments may be combined.

In order to recapitulate the above described embodiments of the present invention one can state:

In accordance with embodiments of the herein disclosed subject matter it is described a stirring device 200 for a biogas fermenter wherein the stirring device 200 is configured for stirring a fermentation material and comprises a shaft 102 rotatable about an axis of rotation and a mounting structure 106 attached to the shaft 102. The mounting structure 106 has a first connection surface 112 and the second connection surface 114 and a stirring element 116 is attached to the first connection surface 112 and the second connection surface 114. The first connection surface 112 and the second connection surface 112 are located at opposite sides of the shaft 102 with the shaft being located between the first connection surface 112 and the second connection surface 114. The stirring element 116 may be configured to be spaced from the shaft 102 when the stirring element 116 is attached to the first connection surface 112 and the second connection surface 114. According to an embodiment, the stirring device 200 is adapted for stirring fermentation material which is subject to dry fermentation.

LIST OF REFERENCE SIGNS

100, 200, 300 stirring device
102 shaft
104 axis of rotation
106 mounting structure
108 first element
110 second element
112 first connection surface
114 second connection surface
116 stirring element
117 first leg
118 opposing surface
119 second leg
120 opposing surface
121 body
122 connection plane
124 first mounting part
126 second mounting part
128 axial direction
130 intermediate part
132 attachment surface
133 circumferential edge of 124 or 126
134 first angular range
136 second angular range
137 surface portion of 112
138 surface portion of 114
139 surface portion of 112
140 surface portion of 114
142, 144 surface portions of 120
146 circumferentially extended portion of 130
148 recess
150 first protrusion
152 circumferential direction
154 extent of 130 at 114
156 second protrusion
160 bolt connection
162 threaded bolt
164 retaining the ring
166 guidance

The invention claimed is:

1. A stirring device, wherein the stirring device is configured for stirring a fermentation material in a biogas fermenter comprising:

a shaft rotatable about an axis of rotation;

a mounting structure attached to the shaft, the mounting structure having a first connection surface and a second connection surface; and a stirring element configured for stirring the fermentation material attached to the first connection surface and the second connection surface;

wherein the first connection surface and the second connection surface are located at opposite sides of the shaft with the shaft being located between the first connection surface and the second connection surface;

the first connection surface and the second connection surface defining a connection plane, the connection plane intersecting the shaft; and each of the first connection surface and the second connection surface comprises two surface portions spaced apart from each other in an axial direction;

wherein the mounting structure comprises:

for each of the first connection surface and the second connection surface, a first mounting part attached to the shaft, a second mounting part attached to the shaft, and an intermediate part extending between the first mounting part and the second mounting part, the intermediate part being spaced from the shaft:

the first mounting part and the second mounting part being spaced apart in the axial direction:

each intermediate part providing one of the first connection surface and the second connection surface; and the first mounting part extending over a first angular range, the second mounting part extending over a second angular range and the first angular range and the second angular range overlap each other.

2. The stirring device according to claim 1, wherein the mounting structure comprises a first element and a second element spaced apart from each other in a circumferential direction about the axis of rotation, the first element having the first connection surface and the second element having the second connection surface.

3. The stirring device according to claim 1, wherein the first connection surface and the second connection surface are spaced from the shaft.

4. The stirring device according to claim 1, wherein the first mounting part, the second mounting part and the intermediate part are separate components; and the intermediate part is attached to the first mounting part and the second mounting part.

5. The stirring device according to claim 1, further comprising:

a first protrusion extending in a circumferential direction over the extent of the intermediate part at its connection surface;

the first protrusion connecting the first mounting part and the intermediate part;

a second protrusion extending in a circumferential direction over the extent of the intermediate part at its connection surface;

the second protrusion connecting the second mounting part and the intermediate part.

6. The stirring device according to claim 1, wherein the intermediate part has a circumferentially extended portion located between the two surface portions of the intermediate part.

7. The stirring device according to claim 6, wherein the circumferentially extended portion comprising a recess, the recess reducing a weight of the intermediate part.

8. The stirring device according to claim 1, wherein the stirring element is spaced from the shaft.

9. The stirring device according to claim 1, wherein the stirring element comprises a first leg, a second leg and a body; the body is connected to the first leg and the second leg; and the first leg is connected to the first connection surface and the second leg is connected to the second connection surface.

10. The stirring device according to claim 1, further comprising:

a guidance configured for defining a position of the stirring element with respect to the first connection surface and the second connection surface if the stirring element is in contact with the first connection surface and the second connection surface.

11. The stirring device according to claim 1, further comprising:

a first form-locked joint between the stirring element and the first connection surface;

a second form-locked joint between the stirring element and the second connection surface.

* * * * *